(12) United States Patent
Ratcliffe

(10) Patent No.: US 7,935,363 B2
(45) Date of Patent: May 3, 2011

(54) COMPOSITE MATERIAL FOR TISSUE REPAIR

(75) Inventor: Anthony Ratcliffe, Del Mar, CA (US)

(73) Assignee: Synthasome, Inc., San Diego, CA (US)

( * ) Notice: Subject to any disclaimer, the term of this patent is extended or adjusted under 35 U.S.C. 154(b) by 225 days.

(21) Appl. No.: 11/637,516

(22) Filed: Dec. 12, 2006

(65) Prior Publication Data

US 2008/0139694 A1    Jun. 12, 2008

(51) Int. Cl.
*A61F 13/00* (2006.01)

(52) U.S. Cl. ........................................ 424/443

(58) Field of Classification Search .................. None
See application file for complete search history.

(56) References Cited

U.S. PATENT DOCUMENTS

| | | | |
|---|---|---|---|
| 5,399,665 A | | 3/1995 | Barrera et al. |
| 5,492,697 A | * | 2/1996 | Boyan et al. ............... 623/16.11 |
| 5,549,904 A | * | 8/1996 | Juergensen et al. ........... 424/423 |
| 5,567,435 A | | 10/1996 | Hubbell et al. |
| 5,709,854 A | | 1/1998 | Griffith-Cima et al. |
| 5,860,948 A | * | 1/1999 | Buscemi ....................... 604/21 |
| 6,123,727 A | | 9/2000 | Vacanti et al. |
| 6,224,893 B1 | | 5/2001 | Langer et al. |
| 6,258,870 B1 | | 7/2001 | Hubbell et al. |
| 6,465,001 B1 | | 10/2002 | Hubbell et al. |
| 6,481,993 B1 | | 10/2002 | Shastri et al. |
| 6,554,867 B1 | | 4/2003 | Joos |
| 6,818,018 B1 | * | 11/2004 | Sawhney ................... 623/11.11 |
| 7,241,846 B2 | * | 7/2007 | Roby ............................ 525/406 |
| 2005/0196377 A1 | * | 9/2005 | Ratcliffe et al. ........... 424/78.31 |
| 2006/0160734 A1 | * | 7/2006 | Kusanagi et al. ............... 514/12 |

FOREIGN PATENT DOCUMENTS

| | | |
|---|---|---|
| WO | WO 93/17669 | 9/1993 |
| WO | WO 94/25080 | 11/1994 |

* cited by examiner

*Primary Examiner* — Michael G Hartley
*Assistant Examiner* — Paul Dickinson
(74) *Attorney, Agent, or Firm* — Carter, DeLuca, Farrell & Schmidt, LLP

(57) ABSTRACT

The present disclosure provides a biocompatible composite and method for its use in repairing tissue defects, including defects in cartilage. The biocompatible composite includes a fibrous polymeric component and a polymerizable agent, which is capable of forming the biocompatible composite in situ at the site of a tissue defect. In embodiments, the repair site at which the biocompatible composite is to be applied may be treated with a priming agent, permitting polymerization of the polymerizable agent to the tissue located at the repair site.

10 Claims, 1 Drawing Sheet

COMPOSITE MATERIAL FOR TISSUE REPAIR

TECHNICAL FIELD

The present disclosure pertains to biocompatible composites which may be formed in situ at the site of a tissue defect and their use in repairing defects in tissue. More specifically, the present disclosure is directed to biocompatible composites including both a fibrous polymeric component in combination with a polymerizable agent such as a polymeric hydrogel for use in repairing defects in tissue, including cartilage.

BACKGROUND

Integration of biomaterials with the body is a longstanding problem in medicine. Lack of proper integration with the body sacrifices implant longevity and function. Hard tissues such as cartilage and bone present particular challenges to integration.

Every year in the U.S. there are about 570,000 traumatic injuries to knee articular cartilage, many the result of sports and recreational activities, and approximately half of these require some sort of surgery to repair. Those with articular cartilage injuries often face a series of subsequent surgical interventions throughout their lifetimes, only to end up receiving a total knee replacement. Over 300,000 procedures to treat cartilage defects were performed in 1999; over 240,000 total knee replacements were performed in the same year. Of the 300,000 procedures that were performed on cartilage defects, over 90% were performed arthroscopically, and on an outpatient basis.

Articular cartilage consists of a dense meshwork of collagen fibers (primarily type II, with lesser amounts of other collagens such as type IV, V, IX and XI), embedded in a high concentration of proteoglycan, primarily aggrecan. Collagen influences the tensile properties of the cartilage while the proteoglycans influence the compressive properties of the cartilage. Cartilage is heterogeneous with depth, with the collagen fibers being particularly dense and oriented at the superficial zone, where higher tensile properties are found, with a more random arrangement in the middle and deeper zones of the cartilage. The tensile modulus of articular cartilage may be from about 1 to about 8 MPa, while the tensile modulus of cartilage in the superficial zone may be from about 8 to about 14 MPa. The compressive modulus of articular cartilage may be from about 0.2 to about 0.9 MPa, and the permeability coefficient of articular cartilage may be from about 2.0 to about 0.15 ($10^{-15}$ m$^4$/Nsec).

Articular damage ranges from mild and asymptomatic to extensive and severely affecting function, and over time it frequently progresses from less to more severe pathology. The Outerbridge classification system is frequently used to provide a grade of cartilage damage, and ranges from softening of the articular cartilage (Grade I), superficial fibrillation (Grade II), deep fissuring and extensive loss of cartilage without exposed bone (Grade III), and loss of cartilage down to exposed bone (Grade IV). Defects less than 2 cm$^2$ are considered small, 2-10 cm$^2$ are moderate, and greater than 10 cm$^2$ are considered large. Cartilage defects have a range of severity (some studies suggest the majority are chondral grade III), and frequently they are present in relatively young individuals.

Treatment options for cartilage defects include debridement, shaving and abrasion arthroplasty, subchondral drilling, microfracture, allograft transplantation, autograft implantation, and autologous cell implantation. These treatments involve one or more of the following: (a) clearing damaged cartilage; (b) invasion of the subchondral bone to induce host repair tissue formation; and/or (c) transplantation of cells or osteochondral plugs. Each treatment has demonstrated some value but each also has significant limitations, which can include safety and supply of allografts, donor site morbidity associated with autograft procedures, expense, and the removal of normal articular cartilage to make regularly shaped defect sites. Patients frequently undergo an extensive physical therapy program, requiring restricted use for long periods of time. Treatments rarely offer repair with rapid restoration of function, and few are designed to address grade III defects.

The adhesion of cartilage to cartilage requires molecular bridging between the cartilage surfaces. Tissue culture conditions with load up to 77 kPa have been used to induce adhesion. A fibrin sealant provides about 29 kPa adhesive strength, and the enzyme tissue transglutaminase provides an adhesive strength of 25 kPa. Pre-treatment of a sealant and/or repair site with chondroitinase AC may achieve a 30%-60% increase in adhesive strength. In vivo integration of new tissue using cell-seeded scaffolds can achieve higher interface strengths, of 286 kPa up to 1.2 MPa after 8 months growth.

A consistent limitation in the current repair procedures is the lack of adhesion to the surrounding tissue. This profoundly limits the strength and durability of these materials, as they do not integrate well with the tissue.

Thus, there remains a substantial need for improvement in the treatment options for tissue defects, including the treatment of cartilage injuries and chronic articular degeneration.

SUMMARY

The present composites for repairing tissue defects include a fibrous polymeric component in combination with a polymeric hydrogel, wherein the hydrogel optionally bonds to tissue at the site of the defect.

In embodiments, the present disclosure provides methods including identifying a tissue defect for repair, applying a fibrous polymeric component in combination with a polymerizable agent to said tissue defect, and reacting the polymerizable agent in the presence of the fibrous polymeric component to form a biocompatible composite in the tissue defect that is optionally bound to tissue at the site of the defect. In some embodiments, the reacting step includes exposing the polymerizable agent to a source of ultraviolet radiation. In other embodiments, a the reacting step does not include exposing the polymerizable agent to a source of ultraviolet radiation, but rather can be chemically induced. In still further embodiments both chemical and ultraviolet radiation can be used.

In embodiments, the tissue defect may be primed with a priming agent, optionally in combination with ultraviolet (UV) radiation, prior to applying the fibrous polymeric component in combination with the polymerizable agent.

The present disclosure also provides methods including identifying a tissue defect for repair, priming the tissue defect surface by treating with a priming agent to create a primed tissue surface, applying a fibrous polymeric component in combination with a polymerizable agent to said tissue defect, and reacting the polymerizable agent with the fibrous polymeric component and the primed tissue surface, in embodiments by exposing the polymerizable agent to a source of ultraviolet radiation, to form a biocompatible composite in the tissue defect that is covalently bound to the tissue defect surface. In embodiments, the step of priming the tissue defect also includes exposing the tissue defect to ultraviolet radiation.

In some embodiments, tissue defect to be treated may be adjacent to extracellular matrix, which includes a plurality of tyrosine residues. In this case, the priming step may include oxidizing the extracellular matrix, so the priming agent includes an oxidizing agent. The resulting primed extracellular matrix includes a plurality of tyrosyl radicals, the polymerizable agent includes an acrylate group capable of reacting with the tyrosyl radicals, and the reacting step includes binding the polymerizable agent to the tyrosyl radicals and crosslinking the polymerizable agent.

In embodiments, the tissue defect may be exposed to an enzyme prior to applying the fibrous polymeric component in combination with the polymerizable agent.

Therapeutic agents may be added to the biocompatible composites of the present disclosure.

Methods for repairing tissue defects, including defects in cartilage and bone, are also provided wherein the fibrous polymeric component and the polymerizable agent are combined to form a biocompatible composite in situ in a living body, including a mammal, such as a human.

BRIEF DESCRIPTION OF THE DRAWINGS

Various embodiments of the present disclosure will be described hereinbelow with reference to the FIGURE wherein.

DETAILED DESCRIPTION OF THE PREFERRED EMBODIMENTS

Figure 1:
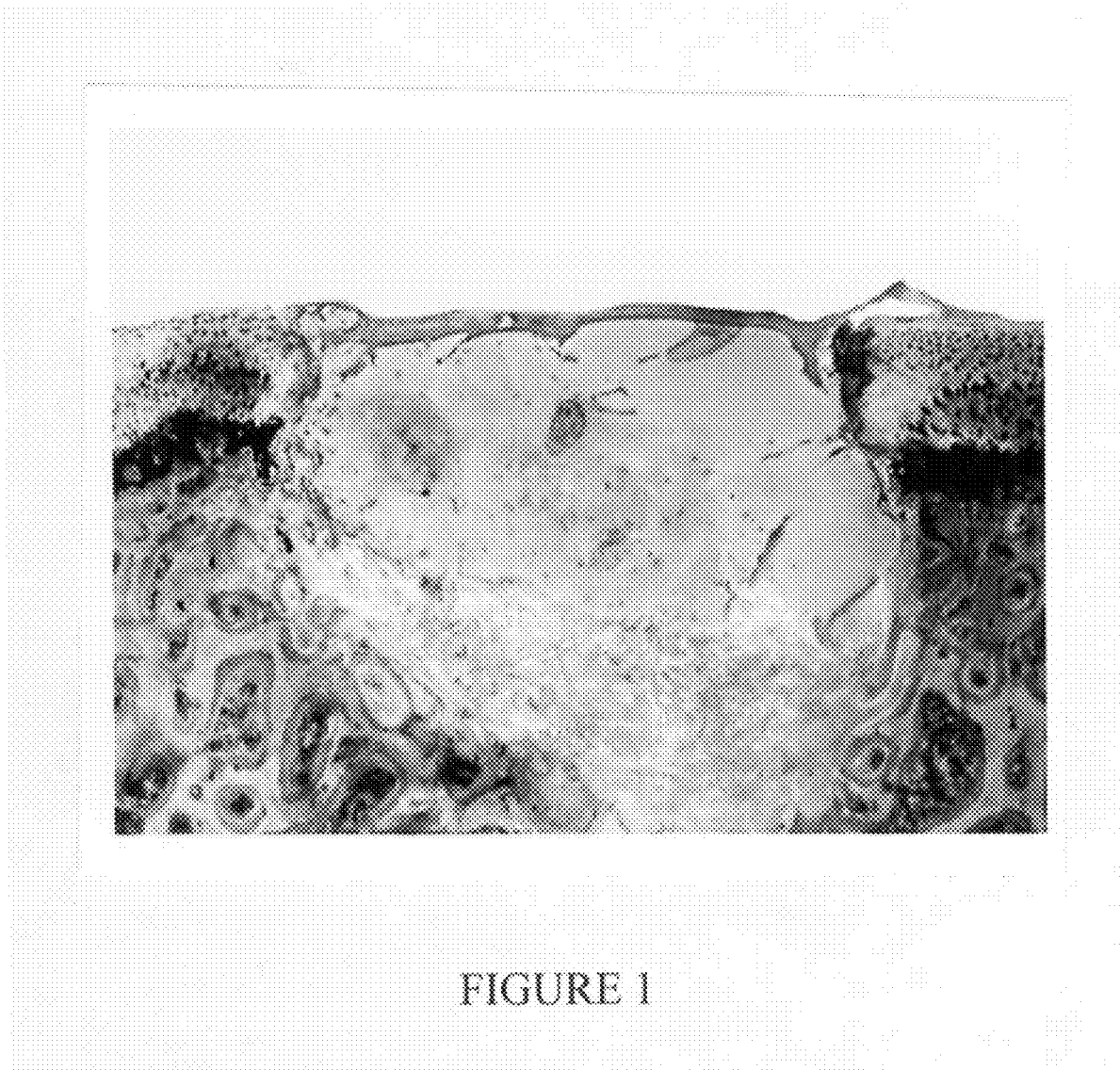
FIG. 1 is an image of a repair of an osteochondral defect in a goat patella with a composite of the present disclosure.

Provided are biocompatible composites including a fibrous polymeric component in combination with a polymerizable agent, such as a polymeric hydrogel, for use in repairing defects in tissue. The biocompatible composite may be formed in vivo, which allows for repair of any shaped defect, does not require the formation of a distinct repair site, and allows for minimally invasive surgery. In embodiments, the biocompatible composite may be used to repair cartilage. In such a case, the biocompatible composite may be formed within a joint to be repaired, does not require the formation of an osteochondral repair site, and may be conducted by a minimally invasive procedure including arthroscopy.

An advantage of certain embodiments of the present disclosure includes the formation of free radicals following localized mild oxidation of the tissue, which enhances the integration of the biocompatible composite with surrounding tissue while eliminating the need for a separate photoinitiator, thereby saving complexity and expense and alleviating any issue of toxicity of the photoinitiator.

The term "hydrogel" as used herein refers to a hydrophilic cross-linked polymer capable of containing a large volume fraction of water. In some embodiments, hydrogels according to the present disclosure can contain greater than about 70-90 volume % water. When a hydrophilic polymer is formed in situ, it may inherently acquire water from its environment or from solutions used to create the hydrogel.

The term "cross-linked" as used herein refers to a composition containing intermolecular cross-links and optionally intramolecular cross-links arising from the formation of covalent bonds, ionic bonds, hydrogen bonding, or any combination thereof. "Cross-linkable" refers to a component or compound that is capable of undergoing reaction to form a cross-linked composition.

As noted above, the biocompatible composite includes a fibrous polymeric component in combination with a polymerizable agent. Non-limiting suitable materials for use as the fibrous polymeric component are within the purview of those skilled in the art and include, but are not limited to, polymeric fibers made of materials including polyhydroxy acids such as polylactic acid (PLA) and polyglycolic acid, polyamino acids, hyaluronic acid, gelatin, cellulose, nitrocellulose, polycaprolactone, polydioxanone, trimethylene carbonate, homopolymers thereof, copolymers thereof, other naturally-occurring biodegradable materials, and combinations thereof.

Other materials which may be used as the fibrous polymeric component include, but are not limited to, polyamides including nylon, polyesters including Dacron and polyethylene terephthalate (PET), polyolefins including polypropylene and polyethylene, polyacrylates, polycarbonates, polytetrafluoroethylene (PTFE), polyhydroxyalkanoates, other non-biodegradable materials, and combinations thereof.

In embodiments, a naturally occurring biodegradable material may be combined with a non-biodegradable material for use as the fibrous polymeric component.

In embodiments, the fibers may be utilized without treatment or processing. In other embodiments, the fibers may be processed into nonwovens, fiber webs, meshes and/or felts. Fiber webs and similar structures may be formed by needling, interlooping, entangling, melting, or sealing of the fibers.

Where the fibrous polymeric component is in the form of a nonwoven, web, mesh or felt, the void volume of such a component may be above about 50% to, in embodiments above about 90% of the component.

Once formed, the fibrous polymeric component may then be used to form a biocompatible composite of the present disclosure by the addition of a polymerizable agent. The polymerizable agent of the present disclosure may include monomers, macromers, oligomers, polymers, or a mixture thereof. The polymerizable agent may include covalently crosslinkable polymers, ionically crosslinkable polymers, polymers crosslinkable by redox chemistry, polymers crosslinked by hydrogen bonding, or any combination thereof. In embodiments, the polymerizable agent may be substantially hydrophilic and biocompatible.

In embodiments the polymerizable agent may be in a solution. As used herein, a "solution" includes a solution, a suspension, and/or a colloid.

The term "biocompatible" is art-recognized. For example, biocompatible polymers include polymers that are neither themselves toxic to the host (e.g., an animal or human), nor degrade (if the polymer degrades) at a rate that produces monomeric or oligomeric subunits or other byproducts at toxic concentrations in the host. In certain embodiments of the present disclosure, biodegradation generally involves degradation of the polymer in an organism, e.g., into its monomeric subunits, which may be known to be effectively non-toxic. Intermediate oligomeric products resulting from such degradation may have different toxicological properties, however, or biodegradation may involve oxidation or other biochemical reactions that generate molecules other than monomeric subunits of the polymer. Consequently, in certain embodiments, toxicology of a biodegradable polymer intended for in vivo use, such as implantation or injection into a patient, may be determined after one or more toxicity analyses. It is not necessary that any subject composition have a purity of 100% to be deemed biocompatible; indeed, it is only necessary that the subject compositions be biocompatible as set forth above. Hence, a subject composition may comprise polymers comprising 99%, 98%, 97%, 96%, 95%, 90%, 85%, 80%, 75% or even less of biocompatible polymers, e.g., including polymers and other materials and excipients described herein, and still be biocompatible.

To determine whether a polymer or other material is biocompatible, it may be necessary to conduct a toxicity analysis. Such assays are within the purview of those skilled in the art. One example of such an assay may be performed with live carcinoma cells, such as GT3TKB tumor cells, in the following manner: the sample is degraded in 1M NaOH at 37° C. until complete degradation is observed. The solution is then neutralized with 1M HCl. About 200 mL of various concentrations of the degraded sample products are placed in 96-well tissue culture plates and seeded with human gastric carcinoma cells (GT3TKB) at 104/well density. The degraded sample products are incubated with the GT3TKB cells for 48 hours. The results of the assay may be plotted as % relative growth vs. concentration of degraded sample in the tissue-culture well. In addition, polymers, polymer matrices, and formulations of the present disclosure may also be evaluated by well-known in vivo tests, such as subcutaneous implantations in rats to confirm that they do not cause significant levels of irritation or inflammation at the subcutaneous implantation sites.

Nonlimiting suitable materials which may be used as the polymerizable agent include those which form hydrogels or hydrophilic polymers such as synthetic polymers such as polyalkylene oxides including poly(ethylene glycol), poly(ethylene oxide), and poly(ethylene oxide)-co-poly(propylene oxide) block copolymers (poloxamers and meroxapols), partially or fully hydrolyzed poly(vinyl alcohol), poly(vinylpyrrolidone), poly(ethyloxazoline), poloxamines, carboxymethyl cellulose, and hydroxyalkylated celluloses such as hydroxyethyl cellulose and methylhydroxypropyl cellulose, and natural polymers such as polypeptides, polysaccharides or carbohydrates such as FICOLL™, polysucrose, hyaluronic acid, dextran, heparan sulfate, chondroitin sulfate, heparin, or alginate, and proteins such as gelatin, collagen, albumin, or ovalbumin or copolymers or combinations thereof. As used herein, "celluloses" includes cellulose and derivatives of the types described above; "dextran" includes dextran and similar derivatives thereof.

Other materials which can be used as the polymerizable agent to form a hydrogel include modified alginates. Alginate is a carbohydrate polymer isolated from seaweed, which can be crosslinked to form a hydrogel by exposure to a divalent cation such as calcium as described, for example, in WO 94/25080, the entire disclosure of which is incorporated herein by this reference. Alginate is ionically crosslinked in the presence of divalent cations, in water, at room temperature, to form a hydrogel matrix. Modified alginate derivatives may be synthesized which have an improved ability to form hydrogels. The use of alginate as the starting material is advantageous because it is available from more than one source, and is available in good purity and characterization. As used herein, the term "modified alginates" refers to chemically modified alginates with modified hydrogel properties. Naturally occurring alginate may be chemically modified to produce alginate polymer derivatives that degrade more quickly. For example, alginate may be chemically cleaved to produce smaller blocks of gellable oligosaccharide blocks and a linear copolymer may be formed with another preselected moiety, e.g. lactic acid or epsilon-caprolactone. The resulting polymer includes alginate blocks which permit ionically catalyzed gelling, and oligoester blocks which produce more rapid degradation depending on the synthetic design. Alternatively, alginate polymers may be used wherein the ratio of mannuronic acid to guluronic acid does not produce a film gel and the alginate polymers may be derivatized with hydrophobic, water-labile chains, e.g., oligomers of epsilon-caprolactone. The hydrophobic interactions induce gelation, until they degrade in the body.

Additionally, polysaccharides which gel by exposure to monovalent cations, including bacterial polysaccharides such as gellan gum, and plant polysaccharides such as carrageenans, may be crosslinked to form a hydrogel using methods analogous to those available for the crosslinking of alginates described above. Polysaccharides which gel in the presence of monovalent cations form hydrogels upon exposure, for example, to a solution comprising physiological levels of sodium. Hydrogel precursor solutions also may be osmotically adjusted with a nonion, such as mannitol, and then injected to form a gel.

Polysaccharides that are very viscous liquids or are thixotropic, and form a gel over time by the slow evolution of structure, may also be useful. For example, hyaluronic acid, which forms an injectable gel with a consistency like a hair gel, may be utilized. Modified hyaluronic acid derivatives may be particularly useful. As used herein, the term "hyaluronic acids" refers to natural and chemically modified hyaluronic acids. Modified hyaluronic acids may be designed and synthesized with preselected chemical modifications to adjust the rate and degree of crosslinking and biodegradation. For example, modified hyaluronic acids may be designed and synthesized which are esterified with a relatively hydrophobic group such as propionic acid or benzylic acid to render the polymer more hydrophobic and gel-forming, or which are grafted with amines to promote electrostatic self-assembly. Modified hyaluronic acids thus may be synthesized which are injectable, in that they flow under stress, but maintain a gel-like structure when not under stress. Hyaluronic acid and derivatives thereof are available from Genzyme, Cambridge, Mass. and Fidia, Italy.

Other polymeric hydrogel precursors which may be utilized include polyethylene oxide-polypropylene glycol block copolymers such as PLURONICS™ or TETRONICS™, which are crosslinked by hydrogen bonding and/or by a temperature change, as described in Steinleitner et al., *Obstetrics & Gynecology*, vol. 77, pp. 48-52 (1991); and Steinleitner et al., *Fertility and Sterility*, vol. 57, pp. 305-308 (1992). Other materials which may be utilized include proteins such as fibrin, collagen and gelatin. Polymer mixtures may also be utilized. For example, a mixture of polyethylene oxide and polyacrylic acid which gels by hydrogen bonding upon mixing may be utilized. In one embodiment, a mixture of a 5% w/w solution of polyacrylic acid with a 5% w/w polyethylene oxide (polyethylene glycol, polyoxyethylene) can be combined to form a gel over the course of time, e.g., as quickly as within a few seconds.

Water soluble polymers with charged side groups may also be utilized and may be crosslinked by reacting the polymer with an aqueous solution containing ions of the opposite charge, either cations if the polymer has acidic side groups or anions if the polymer has basic side groups. Examples of cations for cross-linking of the polymers with acidic side groups to form a hydrogel are monovalent cations such as sodium, divalent cations such as calcium, and multivalent cations such as copper, calcium, aluminum, magnesium, strontium, barium, tin, and di-, tri- or tetra-functional organic cations such as alkylammonium salts. Aqueous solutions of the salts of these cations may be added to the polymers to form soft, highly swollen hydrogels and membranes. The higher the concentration of cation, or the higher the valence, the greater the degree of cross-linking of the polymer. Additionally, the polymers may be crosslinked enzymatically, e.g., fibrin with thrombin.

Nonlimiting suitable ionically crosslinkable groups include phenols, amines, imines, amides, carboxylic acids, sulfonic acids and phosphate groups. Negatively charged groups, such as carboxylate, sulfonate and phosphate ions, can be crosslinked with cations such as calcium ions. The crosslinking of alginate with calcium ions is an example of this type of ionic crosslinking. Positively charged groups, such as ammonium ions, can be crosslinked with negatively charged ions such as carboxylate, sulfonate and phosphate ions. In embodiments, the negatively charged ions contain more than one carboxylate, sulfonate or phosphate group.

Suitable anions for cross-linking of the polymerizable agent to form a hydrogel include monovalent, divalent or trivalent anions such as low molecular weight dicarboxylic acids, for example, terephthalic acid, sulfate ions and carbonate ions. Aqueous solutions of the salts of these anions may be added to the polymers to form soft, highly swollen hydrogels and membranes, as described with respect to cations.

A variety of polycations can be used to complex and thereby stabilize the polymer hydrogel into a semi-permeable surface membrane. Examples of materials that can be used include polymers having basic reactive groups such as amine or imine groups, and having a molecular weight from about 3,000 to about 100,000, such as polyethylenimine and polylysine. These are commercially available. One polycation is poly(L-lysine); examples of synthetic polyamines include polyethyleneimine, poly(vinylamine), and poly(allyl amine). There are also natural polycations such as chitosan, a polysaccharide.

Polyanions that can be used to form a semi-permeable membrane by reaction with basic surface groups on the hydrogel include polymers and copolymers of acrylic acid, methacrylic acid, and other derivatives of acrylic acid, polymers with pendant $SO_3H$ groups such as sulfonated polystyrene, and polystyrene with carboxylic acid groups. These polymers can be modified to contain active species polymerizable groups and/or ionically crosslinkable groups. Methods for modifying hydrophilic polymers to include these groups are within the purview of those skilled in the art.

The term "active species polymerizable group" includes a reactive functional group that has the capacity to form additional covalent bonds resulting in polymer interlinking upon exposure to active species. Active species include free radicals, cations, and anions. Suitable free radical polymerizable groups include ethylenically unsaturated groups (i.e., vinyl groups) such as vinyl ethers, allyl groups, unsaturated monocarboxylic acids, unsaturated dicarboxylic acids, and unsaturated tricarboxylic acids. Unsaturated monocarboxylic acids include acrylic acid, methacrylic acid and crotonic acid. Unsaturated dicarboxylic acids include maleic, fumaric, itaconic, mesaconic or citraconic acid. In one embodiment, the active species polymerizable groups may be located at one or more ends of the hydrophilic polymer. In another embodiment, the active species polymerizable groups may be located within a block copolymer with one or more hydrophilic polymers forming the individual blocks. Suitable polymerizable groups include acrylates, diacrylates, oligoacrylates, dimethacrylates, oligomethacrylates, combinations thereof, and other biologically acceptable photopolymerizable groups. In some embodiments, it may be useful to use acrylates as the active species polymerizable group.

The hydrogels may be intrinsically biodegradable, in some embodiments of low biodegradability (for predictability of dissolution) but of sufficiently low molecular weight to allow excretion. The maximum molecular weight to allow excretion in human beings (or other species in which use is intended) will vary with polymer type, but may often be about 20,000 daltons or below. In some embodiments other polymers which may be used include water-soluble natural polymers and synthetic equivalents or derivatives, including polypeptides, polynucleotides, and degradable polysaccharides.

The hydrogels can be a single block with a molecular weight of at least about 600, in embodiments about 2000 or more, in other embodiments at least about 3000. Alternatively, the hydrogels can include two or more water-soluble blocks which are joined by other groups. Such joining groups can include biodegradable linkages, polymerizable linkages, or both. For example, an unsaturated dicarboxylic acid, such as maleic, fumaric, or aconitic acid, can be esterified with hydrophilic polymers containing hydroxy groups, such as polyethylene glycols, or amidated with hydrophilic polymers containing amine groups, such as poloxamines.

In embodiments, covalently crosslinkable polymerizable agents as hydrogel precursors may be useful. For example, a water soluble polyamine, such as chitosan, can be cross-linked with a water soluble diisothiocyanate, such as polyethylene glycol diisothiocyanate. The isothiocyanates will react with the amines to form a chemically crosslinked gel. Aldehyde reactions with amines, e.g., with polyethylene glycol dialdehyde also may be utilized. A hydroxylated water soluble polymer also may be utilized.

Alternatively, hydrogels may be utilized which include substituents which are crosslinked by a radical reaction upon contact with a radical initiator. For example, polymers including ethylenically unsaturated groups which can be photochemically crosslinked may be utilized, as disclosed in WO 93/17669, the entire disclosure of which is incorporated herein by reference. In this embodiment, water soluble macromers that include at least one water soluble region, a biodegradable region, and at least two free radical-polymerizable regions, may be provided. The macromers may be polymerized by exposure of the polymerizable regions to free radicals generated, for example, by photosensitive chemicals and or light. Examples of these macromers include PEG-oligolactyl-acrylates, wherein the acrylate groups may be polymerized using radical initiating systems, such as an eosin dye, or by brief exposure to ultraviolet or visible light. Additionally, water soluble polymers, including cinnamoyl groups which may be photochemically crosslinked, may be utilized as disclosed in Matsuda et al., *ASAIO Trans.*, vol. 38, pp. 154-157 (1992).

In embodiments, a crosslinking agent may also be added to the fibrous polymeric component and the polymerizable agent to enhance formation of the biocompatible composite of the present disclosure in situ. Such crosslinking agents are within the purview of those skilled in the art and include, for example, aldehydes including glutaraldehyde, imides including carbodiimide, free radical initiators including 2,2'-Azobis (N,N'dimethyleneisobutyramidine) dihydrochloride, benzoyl peroxide, trimethylol propane (TMP), and combinations thereof. The crosslinking agent selected will depend upon the reaction chemistry of the fibrous polymeric component and the polymerizable agent.

In general, the polymerizable agent used to form the hydrogels may be at least partially soluble in aqueous solutions, such as water, buffered salt solutions, or aqueous alcohol solutions. Methods for the synthesis of the other polymeric hydrogels described above are within the purview of those skilled in the art. See, for example Concise Encyclopedia of Polymer Science and Polymeric Amines and Ammonium Salts, E. Goethals, editor (Pergamen Press, Elmsford, N.Y. 1980). Many polymers, such as poly(acrylic acid), are commercially available.

Naturally occurring and synthetic polymers may be modified using chemical reactions available in the art and described, for example, in March, "Advanced Organic Chemistry," 4th Edition, 1992, Wiley-Interscience Publication, New York. Such methods may be used to, for example, introduce acrylate groups as described herein.

The hydrophilic polymers that include active species or crosslinkable groups may include at least about 1.02 polymerizable or crosslinkable groups on average, and, in some embodiments, each may include about two or more polymerizable or crosslinkable groups on average. Because each polymerizable group will polymerize into a chain, crosslinked hydrogels can be produced using only slightly more than one reactive group per polymer (i.e., about 1.02 polymerizable groups on average). However, higher percentages may be desirable, and excellent gels can be obtained in polymer mixtures in which most or all of the molecules have two or more reactive double bonds. Poloxamines, an example of a hydrophilic polymer, have four arms and thus may readily be modified to include four polymerizable groups.

In embodiments, it may be desirable to include a therapeutic agent in the polymerizable agent utilized to form a hydrogel. Such therapeutic agents may include, for example, growth factors proteins, polysaccharides, nucleic acid molecules, and synthetic organic or inorganic molecules including drugs which may be useful for therapeutic, prophylactic, diagnostic purposes, or medicinal. Drugs which may be utilized include antibiotics, antivirals, chemotherapeutic agents, anti-angiogenic agents, hormones, drugs having an effect on vascular flow, anti-inflammatories, and many others routinely used.

In embodiments, the polymerizable agent may include two or more polymers, which may crosslink to form a semi-interpenetrating network. For example, the blend could include PEO, which is ionically crosslinkable, and diamethacrylated PEO, which is covalently crosslinkable, in amounts of about 10 to about 40% by weight. Alternatively, blends of two covalently crosslinkable polymers can be used, selected on the basis that they form a network of crosslinked homopolymers, not to each other. Advantages of the semi-interpenetrating networks include the diffusion of non-crosslinked polymer, which can provide advantageous degradation properties.

The amount of polymerizable agent may vary in amounts of about 5% by weight to about 45% by weight of a solution including the polymerizable agent, in embodiments about 10% by weight to about 40% by weight of the solution, in some embodiments about 20% by weight to about 35% by weight of the solution.

Once the fibrous polymeric component and the polymerizable agent are in place at the tissue defect to be repaired, they may be subjected to radiation to enhance formation of the biocompatible composite of the present disclosure in situ. Suitable radiation treatments are within the purview of those skilled in the art and include, but are not limited to, ultraviolet (UV) radiation. The radiation treatment may enhance polymerization of the polymerizable agent with itself and the fibrous polymeric component to form a biocompatible composite of the present disclosure.

In embodiments, the fibrous polymeric component and the polymerizable agent may be subjected to radiation at an intensity of in amounts of about 2 mW/cm$^2$ to about 20 mW/cm$^2$, in embodiments in amounts of about 3 mW/cm$^2$ to about 10 mW/cm$^2$, in yet other embodiments in amounts of about 4 mW/cm$^2$ to about 6 mW/cm$^2$. Suitable periods of time for this radiation treatment may be about 2 minutes to about 60 minutes, in embodiments about 4 minutes to about 20 minutes, in yet other embodiments about 5 minutes to about 15 minutes.

In embodiments, the radiation treatment may also enhance polymerization of the polymerizable agent with tissue located at the repair site, thereby enhancing both the formation of the biocompatible composite of the present disclosure in situ and its adherence with tissue located at the repair site. Any technique can be employed to covalently bond the hydrogel to tissue, including but not limited to the techniques disclosed in the application published as Publication No. US20050196377A1 entitled Method and Material for Enhanced Tissue-biomaterial Integration, and the international application published as PCT Publication No. WO 2004/029137A2 entitled Cross-linked Polymer Matrices, and Methods of Making and Using Same. The entire disclosures of these two applications are incorporated herein by this reference.

In another embodiment, the biocompatible composite can be formed by the polymerization of the fibrous polymeric component and the polymerizable agent without radiation. Suitable agents to induce polymerization of the fibrous polymeric component and the polymerizable agent include chemical agents such as reducing agents and oxidizing agents. Suitable oxidizing agents include ascorbic acid, sodium ascorbate, magnesium ascorbate-2-phosphate, and sodium thiosulfate. Suitable reducing agents, include ammonium peroxosulfate, sodium peroxosulfate, potassium peroxosulfate, and hydrogen peroxide.

A biocompatible composite of the present disclosure may include the fibrous polymeric component in an amount of about 5% to about 90% by weight of the biocompatible composite, in other embodiments of about 30% to about 75% by weight of the biocompatible composite.

In embodiments, a biocompatible composite of the present disclosure may include the polymerizable agent in an amount of about 95% to about 10% by weight of the biocompatible composite, in other embodiments about 70% to about 25% by weight of the biocompatible composite.

Where it is desirable for the polymerizable agent to polymerize with tissue at the site of the defect to be repaired, it may be desirable to pretreat the site of the defect with a priming agent to improve the ability of the polymerizable agent to polymerize with the tissue. For example, where the biocompatible composite is to be used to repair cartilage, the priming step may permit the polymerizable agent used in forming the biocompatible composite to form covalent bonds between the polymerizable agent and collagen or other matrix proteins at the repair site, thereby providing a mechanism for stable and permanent interaction between the biocompatible composite implant and the surrounding host tissue, including articular cartilage. For example, tyrosine residues on protein form tyrosyl radicals after mild oxidation. See, Qian, et al., Identification of Protein-Derived Tyrosyl Radical in the Reaction of Cytochrome C and Hydrogen Peroxide: Characterization by Esr Spin-Trapping, Hplc and Ms. Biochem J, 2002. 363(Pt 2): p. 281-8.

Nonlimiting suitable priming agents are within the purview of those skilled in the art and include, for example, oxidizing agents and the like. Nonlimiting suitable oxidizing agents include hydrogen peroxide, citric acid, peracetic acid, nitric acid, peroxyhalogen acids, hydroxyperoxides, combinations thereof, and the like.

The concentration of an oxidizing agent used to treat the tissue defect may be in amounts of about 0.1 mM to about 300 mM, in embodiments in amounts of about 50 mM to about 250 mM, in other embodiments in amounts of about 100 mM to about 200 mM.

In some embodiments, it may be desirable to apply a priming agent in combination with additional treatments, including photo-oxidation under UV irradiation. This exposure to UV radiation to enhance oxidation of the tissue, sometimes referred to herein as a UV treatment, is separate from the UV polymerization described above whereby UV radiation enhances the polymerization of the polymerizable agent in forming the biocompatible composite and optionally linking the biocompatible composite with tissue at the site of the defect being repaired. Suitable times for exposure to UV radiation during the oxidative treatment may be about 1 minute to about 30 minutes, in embodiments about 5 minutes to about 15 minutes.

In addition, in embodiments it may be desirable to subject the site of a tissue defect to an enzymatic treatment to further enhance polymerization of the polymerizable agent with the host tissue at the site of the defect to be repaired. Nonlimiting suitable enzymes include, for example, chondroitinases and the like. In embodiments, for example where the biocompatible composite of the present disclosure is to be used to repair a defect in cartilage, it may be desirable to expose the defect to be treated with an enzyme such as a chondroitinase, including chondroitinase ABC, chondroitinase AC, chondroitinase AC II, chondroitinase AC III, chondroitinase B, and the like, to remove proteoglycans and expose collagen at the site of the defect, thereby enhancing the ability of the polymerizable agent to polymerize with tissue at the site of the defect.

The amount of enzyme applied may be in amounts of about 0.2 U/ml to about 10 U/ml.

Methods of Implantation

A range of different biomaterials may be used as the fibrous polymeric component and the polymerizable agent, each possessing different mechanical properties and different degradation rates. Thus, biocompatible composites of the present disclosure may be utilized to repair a wide variety of tissue defects.

The fibrous polymeric component and the polymerizable agent may be combined in situ by any suitable technique. Where the fibrous polymeric component is in the form of a mesh, felt, web, and the like, the fibrous polymeric component may be cut to the desired shape for placement into the tissue defect, and the polymerizable agent applied thereto. The combination is then positioned at the site of a tissue defect and allowed to crosslink in situ, thereby forming the biocompatible composite of the present disclosure. The fibrous polymeric component and the polymerizable agent may be applied simultaneously or in any order. For example, the polymerizable agent may be applied to a tissue defect followed by the application of the fibrous of polymeric component, and then crosslinked in situ. In embodiments, the fibrous polymeric component may be applied to a tissue defect followed by the application of the polymerizable agent, and then crosslinked in situ. In other embodiments, the polymerizable agent may be applied to a tissue defect followed by the application of the fibrous polymeric component, followed by the application of additional polymerizable agent, and then crosslinked in situ. Any combinations of polymerizable agent and fibrous polymeric component may be utilized to correct a tissue defect; multiple applications of the polymerizable agent and fibrous polymeric component may occur, in embodiments forming multiple layers, which may then be allowed to cross-link in situ to correct a tissue defect.

In other embodiments, a polymerizable agent and fibrous polymeric component may be combined ex vivo and allowed to cross-link, with the resulting biocompatible composite then implanted at the site of a tissue defect to correct same.

As both the fibrous polymeric component and the polymerizable agent may be passed through about a 5 mm hole, the components may be introduced to the site of a tissue defect arthroscopically, or by similar means, including by catheter, laparoscope, thoracoscope, and the like, further minimizing trauma to the patient.

One could also apply an external mold to shape the fibrous polymeric component and the polymerizable agent. Additionally, by controlling the rate of polymerization, it may be possible to mold the biocompatible composite of the present disclosure similar to how one would mold clay.

In embodiments, the biocompatible composite may be introduced into an area wherever a bulking agent is desired, i.e., a soft tissue deformity such as that seen with areas of muscle atrophy due to congenital or acquired diseases, or secondary to trauma, burns, and the like. An example of this would be the introduction of the fibrous polymeric component and the polymerizable agent in the upper torso of a patient with muscular atrophy secondary to nerve damage.

The biocompatible composite can also be introduced as a bulking agent for hard tissue defects, such as bone or cartilage defects, either congenital or acquired disease states, or secondary to trauma or burns. An example of this would be the introduction of the fibrous polymeric component and the polymerizable agent into the area surrounding the skull where a bony deformity exists secondary to trauma.

The fibrous polymeric component and the polymerizable agent could also be introduced to a site of a tissue defect through a catheter having a sufficiently large exit opening, optionally with fluoroscopic, sonographic, computed tomography, magnetic resonance imaging, or other type of radiologic guidance. This would allow for placement of the fibrous polymeric component and the polymerizable agent to specific organs or other tissue regions in the body, wherever a bulking agent would be required.

Further, the fibrous polymeric component and the polymerizable agent could be introduced through a laparoscope or thoracoscope having a sufficiently large exit opening, to any intraperitoneal or extraperitoneal or thoracic organ. For example, the fibrous polymeric component and the polymerizable agent could be introduced in the region of the gastroesophageal junction for the correcting of gastroesophageal reflux. This could be performed either with a thoracoscope introducing the substance in the esophageal portion of the gastroesophageal region, or via a laparoscope by injecting the substance in the gastric portion of the gastroesophageal region, or by a combined approach.

The fibrous polymeric component and the polymerizable agent can also be applied during the course of reconstructive surgery, as well as anywhere in the human body where a biocompatible material is necessary. The fibrous polymeric component and the polymerizable agent can be introduced endoscopically, for example through a laryngoscope, for injection into the vocal chords for the treatment of dysphonia, or through a hysteroscope for injection into the fallopian tubes as a method of rendering the patient infertile, or through a proctoscope, for injection of the substance in the perirectal sphincter area, thereby increasing the resistance in the sphincter area and rendering the patient continent of stool.

Tears in fibrocartilage and soft tissue, especially meniscal tears including peripheral meniscal tears, may be repaired by application of compositions in accordance with the present disclosure to the site of the tear and thereby covalently binding the polymerizable agent to the fibrocartilage or soft tissue. Typically, a tear in the vascular region of the meniscus is repaired using arthroscopic techniques. An instrument for application of the present compositions may be inserted through small incisions which serve as anterior knee portals. Sutures or clips may be passed through a meniscal repair instrument and through the meniscus as a supplemental support to maintain the torn edges in an approximated position. The use of the present compositions that include a polymerizable agent reapproximates the torn edges of the meniscus and allows for healing of the tear.

In another embodiment, the present compositions may be used to repair tears or defects in periosteum. Such defects in the periosteum frequently occur around bone fracture sites where it is usually destroyed and cannot serve as a membrane barrier against the dislocation of bone fragments. By application of compositions in accordance with the present disclosure to the site of the tear or defect, and thereby covalently binding the polymerizable agent to the periosteum, repair and/or regrowth of the periosteum can be achieved. Morphogenic proteins may also be combined with the fibrous polymeric component, the polymerizable agent, or both, which attract mesenchymal stem cells from the periosteum. The attracted elements are then directed to differentiate into bone forming cells, which are essential for new bone formation by the patient. Thus, by repairing the periosteum, the present compositions and methods may also assist in the regeneration of defects in bone.

In another embodiment, the present compositions may be used to attach periosteum and other extracellular matrices to cartilage, as part of a cartilage repair method. Cartilage defects frequently occur within diarthrodial joints, and a prior method used to attempt to repair these includes the implantation of cells into the defect site, and attachment of periosteum or other extracellular matrices over the defect site, by suturing in place. The suturing method is difficult and can damage the surrounding articular cartilage. By application of compositions in accordance with the present disclosure, wherein the polymerizable agent combines with the fibrous polymeric component and covalently attaches to the periosteum and cartilage, a repair of the articular cartilage may be achieved by formation of the biocompatible composite in situ.

In another embodiment, the present compositions may be used to attach preparations of subintestinal submucosa and other extracellular matrices to a tendon or ligament, as used to enhance repair of these tissues. Tendon and ligament tears frequently occur, for example in the rotator cuff of the shoulder, and surgical repair is used suturing the rotator cuff together and to the bone, with the inclusion of a subintestinal submucosa or other extracellular matrix preparations over the repair site, to enhance the repair. However, prior methods suture these materials in place, providing poor physical attachment over much of the repair area. By application of compositions in accordance with the present disclosure thereby forming a biocompatible composite in situ and adhering same to the rotator cuff, and optionally covalently attaching the polymerizable agent to any subintestinal submucosa or other extracellular matrix preparations which may also be used in repairing the defect, an improved repair may be achieved.

In some embodiments, the biocompatible composites of the present disclosure may be designed to possess compressive and tensile properties within the range of native articular cartilage and thus may be utilized to form a functional repair of a chondral defect, which may involve binding the biocompatible composite constructs of the present disclosure to articular cartilage surrounding the chondral defect. Moreover, covalent bonds between the polymerizable agent and host cartilage can be established, thus adhesion of the biocompatible composite to host cartilage can be achieved with tensile strength in the range of normal articular cartilage, without compromising cell viability. The biocompatible composite of the present disclosure may also be used for femoral chondyle repair.

The biocompatible composite of the present disclosure may also be used to attach cartilage to bone, bone to bone, and in the repair of bone defects. Other tissues which may be repaired with a composite of the present disclosure include, but are not limited to, ligaments, tendons, skin, muscle, fascia, breast tissue, and the like. The biocompatible composite of the present disclosure exhibits resiliency to repeat and extensive loading.

The present disclosure will now be described with reference to certain instructive, non-limiting examples.

Example 1

A biocompatible composite construct was used to repair a chondral articular defect. To determine the feasibility of assembling the biocompatible composite construct in situ, the articular surface of a calf knee femoral chondyle was exposed and a chondral defect with a diameter of 10 mm and depth of 2 mm was created on the articular surface, using a 10 mm diameter drill. (The depth of the bovine articular cartilage was approximately 2.5-3.0 mm.) A disc of PLA-felt (OD=10 and thickness=2 mm) was soaked in hydrogel (18.5%) and placed in the defect site. The remaining spaces between the fibers at the defect site were filled with hydrogel before exposure to UV (10 mW/cm$^2$ for 10 minutes).

This method resulted in the assembly of a crosslinked biocompatible composite construct within the chondral defect of calf articular cartilage, thereby completely repairing the defect. The construct was completely attached to the surrounding tissue and easily stood its own weight. The surface of the construct was smooth and there was no gap between the construct and surrounding articular cartilage. The construct was then cut and removed from the defect site and examined. The cross section of the construct illustrated that it obtained a curvature that matched the architecture of the articular cartilage surface at the defect site.

A similar experiment was conducted to repair a defect in a larger femoral chondyle defect in situ. The femoral chondyle defect to be repaired was an irregular defect of approximately 2.5 cm×2 cm (500 mm$^2$); a PET felt disc was prepared as described above for implantation by immersion in a hydrogel. The combination of the PET felt disc and hydrogel were subjected to UV radiation as described above, which resulted in a complete repair of the chondyle defect with the construct, with the repair site possessing a smooth surface and contour which matched the area of the chondyle that was being restored.

Example 2

A PET felt and PEG hydrogel are selected as materials used to form a biocompatible composite by embedding the felt in a 10% polyethylene glycol diacrylate solution polymerized using UV light (10 mW/cm$^2$ for 300 seconds). Both materials are regarded as non-degradable, and are currently being used in FDA-approved devices. The non-degradable feature allows for the potential of relatively long term function of the biocompatible composite. The use of materials in already approved products provides an excellent safety profile, removing a major area of potential concern.

The compressive modulus, permeability, and tensile modulus of the biocompatible composite construct are all within the range of normal articular cartilage. The mechanical properties of the biocompatible composite may be optimized to approach those of native articular cartilage, using a Design of Experiment (DOE) approach. This involves a factorial design, using a commercial software package, DESIGN-EXPERT® from Stat-Ease, Inc. (Minneapolis, Minn.).

Three factors considered most influential on the mechanical properties of the constructs are controlled in the experiments: PET-felt void fraction, PEGDA concentration, and UV polymerization time; the operating ranges of interest are shown below in Table 1. The DOE study is performed with 3 variables, using low, center and high points for each variable.

TABLE 1

| Factors (Controlled Variables) | Units | Factor Levels | | |
|---|---|---|---|---|
| | | Low | Center | High |
| PET-Felt Void Fraction | % | 93 | 95 | 97 |
| PEGDA Concentration | % | 20 | 25 | 30 |
| UV Polymerization Time | Min. | 5 | 10 | 15 |

A two-level, full ($2^K$) factorial design, with 2 replicates and 3 center points, are used to identify the parameters that are most influential on tensile and compressive properties of the constructs. The design results in 19 conditions being used in this experiment. This DOE study allows main effects and factor interactions to be clear of any aliases. Also, two and three factor interactions are generated and therefore factor interactions are determined. Additionally, the center points are an indication of non-linearity effects of the factors on the outcome measures. A power calculation indicates that there is about a 95.3% chance of detecting an effect the size of 2 standard deviations.

The constructs undergo mechanical testing to determine tensile and compressive properties, and the following parameters are regarded as the primary outcome measures: tensile modulus, compressive modulus, and permeability. Results obtained from the DOE study are analyzed by ANOVA using DESIGN-EXPERT®, and significance of the major factors and factor interactions is based on $p \leq 0.05$.

Some of the factors and combination of the factors are expected to contribute significantly to the resultant outcome measures. Analysis of the results determine the magnitude and directionality of these effects and allow one to select a formulation to be tested in a confirmatory experiment to determine the accuracy of the selected values for each influential parameter to be used in a comparative study.

Constructs with properties similar to native articular cartilage have the target ranges set forth below in Table 2.

TABLE 2

| Tensile modulus | Compressive modulus (Mpa) | Permeability ($10^{-15}$ m$^4$/N-s) |
|---|---|---|
| 1.0-8 MPa | 0.2-0.8 | 2.0-0.15 |

Example 3

The adhesion of the biocompatible composite construct to cartilage may be further optimized. Differences between nasal and articular cartilage, and between hydrogel and a fiber hydrogel, may be utilized to form the basis of a new optimization study. The DESIGN-EXPERT® software is used to design a DOE study for articular cartilage with the objective to identify the most influential parameters and their optimal operating ranges for adhering native articular cartilage to hydrogel-fiber constructs. Since one mechanism for the reaction of cartilage with the hydrogel has been demonstrated to be through tyrosine residues in collagen, the surface of cartilage is enzymatically treated with chondroitinase to remove proteoglycans and expose collagen.

A DOE study is performed to identify general treatment parameters for enzymatic and oxidative treatments. It is acknowledged that these may interact, and therefore the data is generated to identify the key parameters. Six factors are used in the DOE study: chondroitinase ABC concentration, peroxide concentration, PEGDA concentration, UV treatment time, UV polymerization time, and presence or absence of PET felt. Table 3 shows the factors and ranges for each factor to be used in this experiment.

TABLE 3

| Factors | | Factor Levels | | |
|---|---|---|---|---|
| (Controlled Variables) | Units | Low | Center | High |
| Chondroitinase ABC Concentration | U/ml | 0 | 5 | 10 |
| Peroxide Concentration | MM | 0 | 150 | 300 |
| PEGDA Concentration | % | 20 | 25 | 30 |
| UV Treatment Time | Min. | 0 | 10 | 20 |
| UV Polymerization Time | Min. | 5 | 15 | 15 |
| PET-Felt Scaffold | Categorical | NO | — | YES |

The outcome measures are: (a) cell viability analysis; (b) surface chemical analysis; and (C) end-to-end tensile mechanical analysis. The experimental design uses 38 conditions that are explored in the two-level $2^{(6-1)}$ half-factorial design with 3 center points. Using the half-factorial design, one can efficiently select the most influential parameters and their ranges which are used to select the final parameters and their exact values. These parameters and their values are confirmed in a confirmatory experiment. It is noted that in this two-level $2^{(6-1)}$ half-factorial DOE study the single factor effect is aliased with 5 other factor interactions. For example, the effect of factor A is aliased with 5 other factors B, C, D, E, and F interactions ([A]=A+BCDEF). However, usually in this kind of model there is only a very low chance of having 4 or 5 factor interactions, therefore the effect reported is mostly due to the contribution of factor [A] and not the 5 other factor interactions [BCDEF]. This allows the use of half-factorial and still examine the effect of each single factor. The DESIGN-EXPERT® software power calculation indicates a 98.4% chance of detecting an effect the size of 2 standard deviations using this study.

Preparation of Articular Cartilage. Articular cartilage blocks (9×5×2 mm$^3$) are harvested from knees (the patella groove) of 1-2 year old skeletally mature adult bovines. Samples are used fresh (for viability assessment) or stored for 24 hours to 96 hours at 4° C. in PBS containing a mixture of antibiotic and antimycotic agents. The cartilage blocks are cut using a die cutter and placed into a Teflon holder, as described above in Example 6, and undergo treatment for tissue-initiated photo polymerization.

Tissue-initiated photo polymerization. The surface of cartilage is enzymatically treated with chondroitinase (0-10 units/ml for 1 hour at 37° C.) to remove proteoglycans and expose collagen. Photo-oxidation of the cartilage surfaces are performed in an open system with 0, 150 or 300 mM $Na_2S_2O_8$ (in PBS) under UV-radiation (365 nm; 5 mW/cm$^2$; UV light, EXFO Acticure® 4000) for 5, 10 or 15 minutes, respectively. Excess peroxide are removed and thoroughly washed off by PBS.

One piece of the cartilage is placed at the end of a holder and the other side of the holder are filled with hydrogel. Pre-argon-bubbled PEGDA solutions (20%, 25% and 30%, w/v in PBS) are added to the cartilage surfaces with photo-initiator Irgacure 2959 (Ciba Specialty Chemicals, Tarrytown, N.Y., 0.05% final concentration). When PET-felt scaffold is present (indicated by "YES" in Table 3), a piece of PET-felt (5 mm width×9 mm length and 2 mm thickness) are placed next to the articular cartilage and the hydrogel are applied to fill the well before exposure to the UV light. The reactants are then exposed to UV-radiation (365 nm; 5 mW/cm$^2$) for polymerization.

Following the polymerization of the gel and end-to-end adhesion of the cartilage to hydrogel or hydrogel-fiber composite, the samples are subjected to mechanical analysis including both tensile testing to measure the peak stress required to separate the two pieces from each other and compression testing, surface chemical analyses using ATR-FTIR to confirm the covalent bonding of the PEGDA to the cartilage tissue, and/or viability analyses using the Live-Dead Assay (Invitrogen) to measure the thickness of the dead tissue in each specimen.

Tensile testing. The tensile properties are determined as described by Williamson, et al., Tensile Mechanical Properties of Bovine Articular Cartilage: Variations with Growth and Relationships to Collagen Network Components. J Orthop Res, 2003. 21(5): p. 872-80. The equilibrium tensile stiffness ($K_t$) and modulus ($E_t$) is calculated by fitting the approximately linear region of the stress-strain curve with the initial length taken as that corresponding to a stress of 0.05 MPa. The dynamic tensile strength ($F_{ult}$) and ultimate stress ($\sigma_{ult}$) are taken as the ultimate load, and that normalized to the original cross-sectional area.

Compression testing. Disks 9.6 mm are cut, the thickness measured, and the sample placed into a confining chamber between two porous stainless steel platens. Static and dynamic confined compression tests are performed. The test sequence consists of applying a 0-15% ramp compression to the sample, allowing the resultant load to relax to equilibrium, followed by application of a series of oscillatory displacements at frequencies ranging from 0.01-0.5 Hz and amplitudes from 1% to 0.3%. The sample is then subjected to additional ramp compressions to 30% and then 45%, and oscillatory tests at the same amplitudes and frequencies conducted at each static offset compression level. The equilibrium confined compression modulus $H_{A0}$, hydraulic permeability at each of the offset compression levels, kp ($\epsilon=0.15$, 0.3, and 0.45), and strain-dependent parameter, M, are determined.

Confirmation of surface reaction. The reaction of the polymer with the cartilage surface is determined chemically using ATR (attenuated total reflectance)-IR and morphologically using SEM. After polymerization and thorough washing of the polymer and cartilage surface, FT-IR spectra of the cartilage surface that is successfully reacted with polymer have additional peaks at 1110 cm$^{-1}$ for ether, 945 cm$^{-1}$ for PEO, and 1730 cm$^{-1}$ for the carbonyl. For morphological analysis, cartilage-hydrogel constructs are frozen and fractured at the polymer-cell interface. When the polymer is chemically reacted with cartilage, the tissue surface is altered compared to control cartilage surfaces that are untreated.

Live-Dead Assay. Potential toxicity to the chondrocytes surrounding the area of treatment and polymer attachment is examined using a Live-Dead Kit (Molecular Probes, Eugene, Oreg.). Treated cartilage samples are exposed to calcein and ethidium homodimer-1 according to the manufacturer's instructions. After washing in PBS to remove excess reagents, a center slice is cut and analyzed using a fluorescent microscope. Pictures are recorded electronically and the extent of non-viable tissue measured by comparison to a stage micrometer (Fisher Scientific).

Results from the design are analyzed by ANOVA using the DESIGN-EXPERT® software and significance of the major variables (factors) and factor interactions are based on $p \leq 0.05$. The analysis provides the optimal solutions for maximizing tensile strength and cell viability.

Example 4

The results obtained in Example 3 are used to design a second DOE study, to optimize the use of biocompatible composites of the present disclosure for the repair of articular cartilage. Analysis of the results obtained in Example 3 allow one to select a smaller set of formulations to be tested in this second DOE study. This experiment optimizes the adhesion strength, cell viability, and minimize the time of the procedure. The targeted outcomes are shown below in Table 4.

TABLE 4

| Peak stress | Cell viability | ATR-FTIR |
|---|---|---|
| >240 KPa | <200 nm depth | Presence of covalent bond |

The peak stress target of 240 kPa is selected as a substantial increase in adhesive strength over previous methods, being three fold higher than the highest value published in the literature, and is about 25% of the lower range of native articular cartilage; in turn, this is within the range of safety factors defined for other musculoskeletal tissues (tendon: 2.5 times to about 10 times, bone: about 1.4 times to about 4 times).

Cell death occurs in cartilage adjacent to a cut surface. Reaction conditions are accepted as compatible if the region of cell death does not extend beyond that seen after cutting cartilage.

Results obtained for the common factors explored in Examples 9 and 10 above (i.e. UV polymerization time, PEGDA concentration, and PET-felt scaffold) may be different. The DESIGN-EXPERT® software provides a ranking of multiple solutions for optimizing the interaction of the parameters in this study, and the optimal matching solution is determined in this Example. This solution is confirmed in a confirmatory experiment.

The experimental processes described in this Example and Examples 2 and 3 above allow one to optimally and accurately determine the value of each influential parameter to develop hydrogel-fiber biocompatible composites in accordance with the present disclosure possessing mechanical properties similar to native articular cartilage. The biocompatible composite may be formed in situ, and can be covalently bound to articular cartilage with maximum adhesive strength and cell viability at the adhesion site. The time of the procedure is minimized with the intent to reduce the impact of the procedure time on the total surgery time and cost.

Example 5

This Experiment demonstrates the formation and attachment of the biocompatible composite device in situ.

The conditions identified in Examples 2-4 are used to determine if the biocompatible composite construct can be assembled within an articular defect in situ, and if the adhesion process keeps the hydrogel-fiber construct in place and prevents the dislocation of the construct. The experimental model system is as described in Example 1 above: a chondral defect (10 mm diameter×2 mm deep) is made in the articular surface of calf knee femoral condyle. The biocompatible composite construct is assembled within the defect site as described above in Example 1, and the adhesion reaction performed under those conditions described in Example 1.

The result is an assembled biocompatible composite construct adhered to the surrounding host articular cartilage. The repair is assessed for (a) mechanical properties of the construct, and (b) adhesive strength to the surrounding host articular cartilage. The composite constructs or construct-cartilage samples are carefully dissected from the repair sites. Constructs are assessed for compressive modulus, permeability, and tensile modulus. The construct-cartilage samples are also tested for adhesive strength and cell viability. The experimental design is shown below in Table 5.

TABLE 5

| Construct analysis | N | Tissue adhesion analysis | N |
|---|---|---|---|
| Tensile testing | 6 | Tensile testing | 6 |
| Compression testing | 6 | Cell viability | 6 |

The objective is to achieve mechanical properties of the construct, and adhesive strength.

Example 6

The methodology and structures described above were assessed to determine their ability to repair tissue defects in vivo. Osteochondral defects (4.5 mm in width, 8 mm depth) were created in the patella groove of goat knees (n=3). PLLA mesh was placed into the defect site, priming was performed, PEG hydrogel was applied and crosslinked, resulting in a completely filled defect site. The goats were allowed normal activity for 4 weeks, killed and the knees harvested. Gross examination and histology showed that the defect sites remained repaired, filled with the hydrogel-scaffold, that was adhered to the surrounding articular and bone tissue. An image of the repair site is shown in FIG. 1.

While the present disclosure has been described with reference to certain embodiments, one of ordinary skill in the art will recognize that additions, deletions, substitutions, modifications and improvements can be made while remaining within the spirit and scope of the present disclosure as defined by the appended claims.

What is claimed is:

1. A method comprising:
   identifying a tissue defect for repair;
   applying a polylactic acid fibrous polymeric component in combination with a polyethylene glycol polymerizable agent to the tissue defect; and
   reacting the polymerizable agent with tissue by exposure to ultraviolet light at the site of the defect in the absence of a priming agent.

2. The method of claim 1, wherein the polyethylene glycol polymerizable agent comprises possessing at least one free radical polymerizable group selected from the group consisting of acrylates, diacrylates, oligoacrylates, dimethacrylates, oligomethacrylates, and combinations thereof.

3. The method of claim 1, wherein the fibrous polymeric component is combined with the polymerizable agent prior to application to the tissue defect.

4. The method of claim 1, wherein the fibrous polymeric component and the polymerizable agent form a biocompatible composite in the tissue defect that is covalently bound to the tissue defect surface.

5. The method of claim 1, further comprises applying a therapeutic agent to the tissue defect.

6. The method of claim 1, further comprising exposing the tissue defect to an enzyme prior to applying the fibrous polymeric component in combination with the polymerizable agent.

7. The method of claim 6, wherein the enzyme comprises a chondroitinase.

8. The method of claim 1, wherein the tissue defect is in cartilage.

9. The method of claim 1, wherein the tissue defect is in tissue selected from the group consisting of bone, ligaments, tendons, skin, muscle and fascia.

10. The method of claim 1, further comprising applying a medicinal agent to the tissue defect.

* * * * *